(12) United States Patent
Legay et al.

(10) Patent No.: US 7,142,924 B2
(45) Date of Patent: Nov. 28, 2006

(54) ACTIVE MEDICAL DEVICE EQUIPPED WITH A MEMORY FOR THE STORAGE OF HOLTER DATA AND OF INSTRUCTIONS FOR CONTROLLING A MICROPROCESSER

(75) Inventors: Thierry Legay, Fontenay les Bris (FR); Karim Amara, Sceaux (FR)

(73) Assignee: ELA Medical S.A.S., Montrouge (FR)

( * ) Notice: Subject to any disclaimer, the term of this patent is extended or adjusted under 35 U.S.C. 154(b) by 391 days.

(21) Appl. No.: 10/846,803

(22) Filed: May 14, 2004

(65) Prior Publication Data
US 2004/0254615 A1   Dec. 16, 2004

(51) Int. Cl.
*A61N 1/00* (2006.01)

(52) U.S. Cl. .............. 607/30; 607/31; 607/2

(58) Field of Classification Search ........... 600/523; 607/30, 31
See application file for complete search history.

(56) References Cited

U.S. PATENT DOCUMENTS

| | | | |
|---|---|---|---|
| 5,306,293 A * | 4/1994 | Zacouto | 607/17 |
| 6,185,696 B1 * | 2/2001 | Noll | 714/6 |
| 6,230,058 B1 * | 5/2001 | Legay | 607/59 |
| 2003/0070054 A1 * | 4/2003 | Williams et al. | 711/173 |

* cited by examiner

*Primary Examiner*—Robert E. Pezzuto
*Assistant Examiner*—Brian T. Gedeon
(74) *Attorney, Agent, or Firm*—Orrick Herrington & Sutcliffe, LLP

(57) ABSTRACT

An active medical device equipped with a memory for the storage of medical data such as Holter data and instructions for controlling a microprocessor. This device comprises a micro-processor operating (14) on N bits, and a memory organized in words of 2N bits, with a first sector (22) storing a control software for the microprocessor, and a second sector (24) storing of the elementary medical data of N bits. Each word of the first sector includes N bits of operating code and n bits of error detection and correction code, with $1 \leq n \leq N$. An interfacing circuit (18) allows, according to commands delivered by the microprocessor, to read in parallel N+n bits of a word from the first sector, or to read or to write N bits of low weight of a word of the second sector, or to read or write N bits of high weight of a word of the second sector.

27 Claims, 1 Drawing Sheet

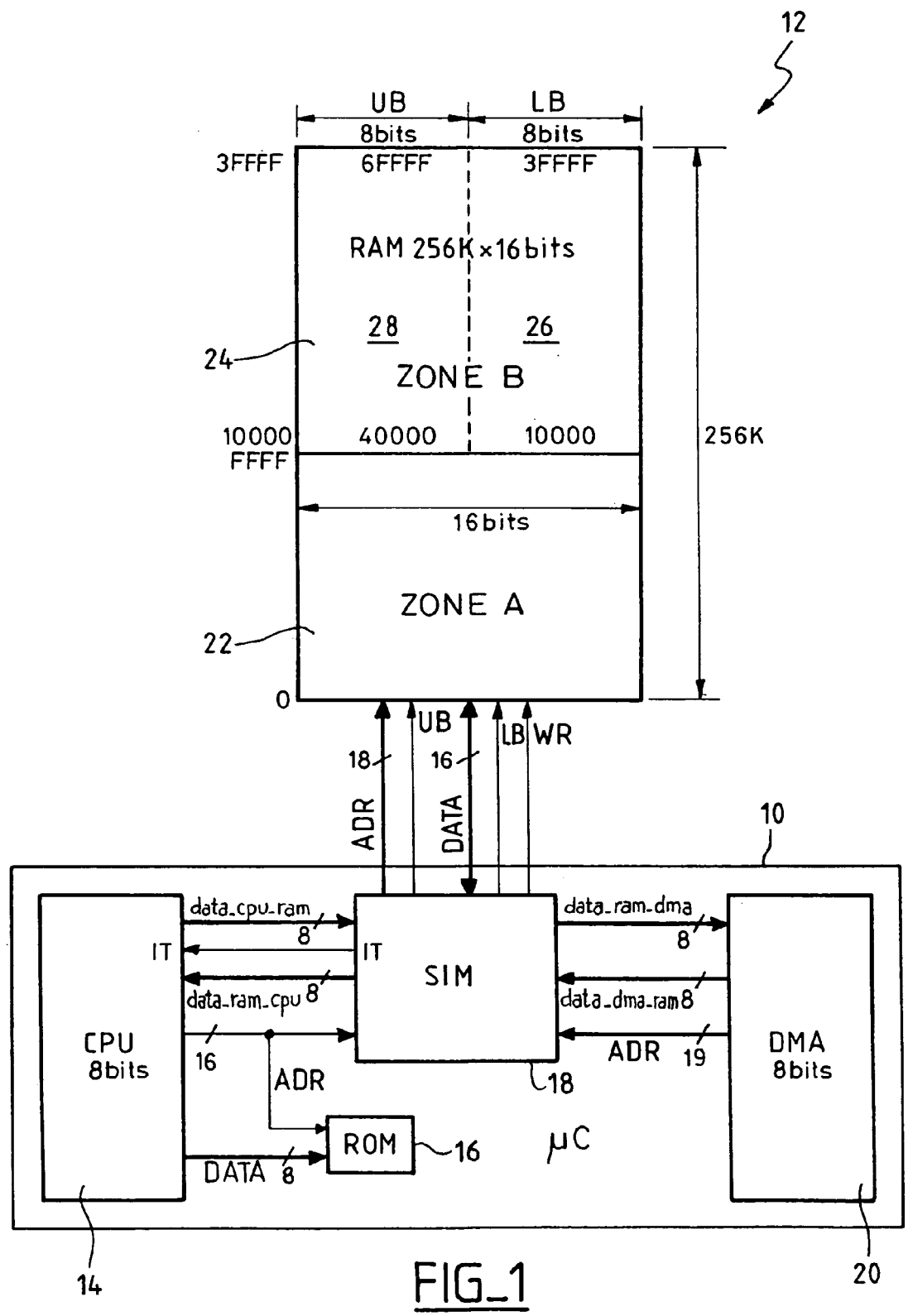
FIG_1

ACTIVE MEDICAL DEVICE EQUIPPED WITH A MEMORY FOR THE STORAGE OF HOLTER DATA AND OF INSTRUCTIONS FOR CONTROLLING A MICROPROCESSER

FIELD OF THE INVENTION

The present invention relates to "active medical devices", and more particularly to "active implantable medical devices" as defined by Directive 90/385/CE of Jun. 20, 1990 of the Council of the European Communities. This definition includes cardiac pacemakers, defibrillators, cardiovertors, cardiac resynchronization devices, and/or multisite devices, as well as neurological devices, pumps for the diffusion of medical substances, cochlear implants, implanted biological sensors, etc., as well as devices for the measurement of pH or for the measurement of intracorporeal impedance (such as the measurement of the transpulmonary impedance or the intracardiac impedance).

The invention applies in a particularly advantageous manner to those devices that implement a function of recording medical data, including in particular the so-called "Holter data", over a long period of time, e.g., from several days to several months. Such recorded data mainly relates to detected cardiac activity but also can include counters of events or not-detected signals that are representative of a state or an action of the implant, for example, the application of a shock therapy, the measurement of an impedance of a probe, etc.

BACKGROUND OF THE INVENTION

The description that follows refers mainly to implanted medical devices such as pacemakers, cardiovertors or defibrillators, but it should be understood that the invention also can be implemented with simple Holter devices, including external devices, for the monitoring and the ambulatory recording of a patient's cardiac activity.

The typical architecture of the electronic circuits of a pacemaker or implantable cardiac defibrillator includes a central processing unit, with a memory of the ROM type (read-only memory) integrated into a microcontroller and containing the software operating code (instructions) making it possible to control the cardiac prosthesis, as well as a memory of the RAM type (read-write random access memory) of larger capacity for the storage of medical data collected (i.e., detected or sensed) by the prosthesis. The circuit architecture also comprises elements suitable for interfacing with the analog circuits (e.g., preamplifiers, filters, signal conditioning circuits, input output interfaces and protection circuits), and eventually a DMA (direct memory access) circuit and different peripheral components necessary to the functioning of the prosthesis.

A first difficulty with this type of classical circuit architecture lies in the difficulty to update the software operating code. Indeed, to update this code an operation known as "remasking" the microcontroller (or microprocessor) is necessary. This operation is done by the manufacturer of the circuit (i.e., at the foundry) and requires a long time, typically from two to three months, to complete. When the new circuit is delivered, it then needs to be incorporated into the prostheses manufacture, which may require two to three additional months to achieve, corresponding to the complete duration of a conventional industrial production cycle. Thus, the time between the development of a new version of the software code and its commercial introduction into products deliverable to the physician is in general of at least six months.

OBJECTS AND SUMMARY OF THE INVENTION

It is therefore an object of the present invention to mitigate this disadvantage by offering an improvement in the flexibility and cycle time for the update of the software code, by way of storage of this software in a RAM circuit rather than in the ROM, but with an adequate protection against corruption and loss. In this regard, a RAM circuit does not present the same guarantees of safety as a ROM circuit, in which the integrity of information stored is guaranteed in any event. For example, the information stored in a RAM circuit can be in particular altered by radiation, such as the alpha particles that can modify in a random manner the state of a bit of information. Such a deterioration is known as Single Event Upset or SEU.

Another object of the invention is to reduce the number of chips (discrete integrated circuits) necessary for the realization of an implantable cardiac prosthesis.

As it is known, the miniaturization of circuits is an essential factor for this type of medical device, and an architecture making it possible to gain surface area on the hybrid circuit carrying the various chips, by decreasing the number of these chips, represents a significant improvement. A goal of the invention is therefore to propose an architecture that makes it possible to use one RAM circuit to store both the software code (with the correlative advantage of an easy update as indicated above) and the acquired medical data such as Holter data.

In addition, it is known that the Holter data recording techniques require significant memory resources if one wants to have both precise data and data covering a lengthy period. Thus, it is desirable to be able to extend the follow-up of a patient to cover a six month duration with a temporal resolution of one day (or less), while recording a significant volume of data and electrograms (EGM) collected (i.e., detected or sensed) immediately proceeding an undesirable event ("EGM pre-event storage"), and after treatment of this same event by the prosthesis, for example, after application of a defibrillation or cardioversion shock, or after a modification of the stimulation mode ("post-event storage").

It is therefore another object of the present invention is to propose an architecture that makes it possible to store in the same device both the software code and the acquired Holter data with extended addressing capacities, independently managed for these two types of information so as to maximize the volume of the stored Holter data.

In other words, the invention has as an aim an architecture allowing, with a minimal surface on the same RAM circuit, to store great quantities of Holter data on the one hand, and to store in a fully secure manner all or part of the software code, on the other hand.

To achieve the various above mentioned objects, the present invention proposes an active medical device comprising, in a manner that is in itself known: a microprocessor; means for acquiring medical data, in particular medical data known as Holter data; a first memory, able to memorize (i.e., record or store) a control software for operating the microprocessor; and a second memory, able to memorize the medical data collected by the acquisition means.

Preferably the first and the second memory are, respectively, a first sector and a second sector of a common single memory component of the rewriteable memory type. In one example, the microprocessor is preferably a device operating on N bits in parallel, the aforementioned memory component is a memory organized in words of 2N bits. The aforementioned control software is then memorized (i.e., stored in memory) in words of 2N bits in the first sector, each one of these words including N bits of operating code ("OC") forming an instruction for controlling the microprocessor, and n bits of error detection and correction code, with $1 \leq n \leq N$. Further, the aforementioned medical data are formed of elementary data of N bits memorized in words of 2N bits in the second sector, each one of these words including N bits of high weight and N bits of low weight, each one memorizing an elementary medical data.

In addition, the device also preferably includes an interfacing circuit, cooperating with the microprocessor and the common memory component and operable, in a selective manner according to commands delivered by the microprocessor: to read or write in parallel the N+n bits of an OC word of the first sector, or to read or write N bits of low weight of a word of the second sector, or to read or write N bits of high weight of a word of the second sector. The interface circuit also can, after reading of N+n bits of a word of the first sector, analyze N bits of the operating code and n bits of the error detection and correction code so as to check the integrity of the operating code, and, only in the event of proven integrity, transmit to the microprocessor N bits of the operating code.

Advantageously, in the event that the integrity of the operating code is not proven, the interface circuit also is able to restore to an integrate (i.e., a correct whole) value the N bits of the operating code starting from n bits of the error detection and correction code, and to transmit to the microprocessor the N bits of the operating code thus restored. In this case, the interface circuit can also re-compute the n bits of the error detection and correction code corresponding to the restored N bits of the operating code, and control the microprocessor so as to rewrite in the first sector the restored N bits of the operating code and the re-computed n bits corresponding to the error detection and correction code.

Very advantageously, the device further includes means for updating the control software of the microprocessor, with means for downloading sequences of words of N bits of operating code instructions for the microprocessor, the interface circuit being then suited, for each downloaded word of N bits, to calculate n bits of the error detection and correction code corresponding to the N bits, and to write in the first sector the N bits and the corresponding n bits of the calculated error detection and correction code.

It is preferably envisaged to provide in addition a read-only memory, distinct from the aforesaid common memory component, containing operating code instructions for controlling the interface circuit for the aforementioned operations of re-calculation and rewriting.

In the event that the integrity of the operating code is not proven and if the device is unable to restore the operating code to an integrate value of N bits starting from n bits of the error detection and correction code, the microprocessor executes advantageously a fallback software routine. The operating code instructions for controlling the microprocessor for the execution of this fallback software routine are preferably contained in a read-only memory distinct from of the aforesaid common memory component.

Preferably, in each word of the first sector, the N bit operating code and the associated n bit error detection and correction code are memorized with mutual interlacing, and the interface circuit is constructed, after reading in the first sector, to de-interlace the N+n bits of a word into N bits of operating code and an associated n bits of error detection and correction code. If the interface circuit carries out rewriting operations in the first sector, the interface circuit can interlace the restored N bits of the operating code and the recomputed n bits corresponding to the error detection and correction code before rewriting in the first sector. Interlacing is a technique that is conventional in the art of error detection and correction.

In yet another embodiment, the device can also include a direct memory access circuit cooperating with the interfacing circuit. The interface circuit then can, in a selective manner according to commands delivered by the direct memory access circuit, read or write the N bits of low weight of a word of the second sector or the N bits of high weight of a word of the second sector, or to read or write the N+n bits of a word of the first sector (this last case corresponding to the downloading of new software code).

In addition, lastly, to reduce consumption, the aforementioned first memory (which stores the control software for the microprocessor) can advantageously be integrated into the same circuit as that of the microprocessor.

BRIEF DESCRIPTION OF THE DRAWING

Further advantages, characteristics and features of the invention will now be described in the detailed discussion of a preferred embodiment of the present invention that follows, made with reference to the annexed drawing, which is a block diagram illustrating the various circuits of an implementation of the invention and the manner in which those circuits interact.

DETAILED DESCRIPTION OF THE INVENTION

With reference to the FIGURE, a microcontroller 10 of an implantable device cooperates with an external memory 12 that is a RAM circuit of large memory capacity integrated in a chip distinct from microcontroller 10. Memory 12 can be a circuit of a traditional type, functioning at a low voltage (1.8 V or less) with a data storage capacity of 128, 256 or 512 K bytes, a capacity sufficient to make it possible to memorize a few tens of minutes of EGM recording, as is typically required by the conventional diagnosis techniques. In the illustrated example, the RAM is a RAM of 512 K bytes, organized physically in 256 K words of 16 bits.

Microcontroller 10 includes a central processing unit (CPU) 14, which in the illustrated example is a "1 byte" circuit, i.e., working on 8 bits in parallel. Central processing unit 14 is interfaced with a read-only memory (ROM) circuit 16 containing the exploitation code for the processor of CPU 14, as well as various elements of software code suitable for the invention as will be disclosed below. Read-only memory 16 is organized in words of 8 bits, addressable on 16 bits. Microcontroller 10 also includes a specific interface module (SIM) 18, suitable for use with the invention, that will be described in detail hereafter and whose general role is to organize the communication between the central processing unit 14 and external memory RAM 12. Microcontroller 10 can also include a direct memory access (DMA) circuit 20, also interfaced with memory RAM 12 by the SIM 18.

Central processing unit 14 has a data bus on 8 bits for the reading of data in RAM (bus data_ram_cpu), and for the writing of data in RAM (bus data_cpu_ram). The same data bus structure exists for the DMA circuit 20 (bus data_ram_dma, and data_dma_ram).

In a manner characteristic of the invention, memory RAM 12 is used for both: (1) the storage of the software code, in a first zone 22. (zone A), with a logical protection managed by the SIM 18, and (2) the storage of medical data, specifically in this embodiment, Holter data, in a second zone 24 (zone B), without logical protection.

Memory 12 is thus shared in two principal zones, A and B. Zone A, reserved for the software code of the program for the functioning of the central processing unit 14, is organized in words of 16 bits, from address 0 to address FFFF (physical and logic addresses). Each word stored in zone A includes N=8 bits of operating code, to which is added an error detecting and correcting code (EDCC) from n=1 to 8 bits.

The nature of the EDCC is variable and selected among the traditional data protection codes used in industry such as parity check, checksum, cyclic redundancy code (CRC), Reed Salomon encoding etc. According to the performance sought in the detection and the correction of error (i.e., the number of bits for which an error is detected and/or corrected). One can use from 1 to 8 bits to store this EDCC. The use of a relatively larger number of bits increases the performance and robustness of the EDCC, but presents the disadvantage of increasing consumption because, for the same number of lines (16 lines), the data bus will include a correspondingly larger number of active lines, and consequently higher losses in the parasitic capacitance of the substrate. In the same regard, the SIM will also consume more energy because the management of the EDCC will be more complex.

Indeed the power consumption of the microcomputer is a factor that must carefully be controlled, because it has a direct impact on the lifespan of an implant, i.e., the number of years of useful life after which an intervention will be necessary to replace the implant.

In one preferred embodiment satisfactory compromise is reached by using 4 bits of EDCC, that makes it possible to have a detection/correction of 1 error per word. This in turn makes it possible to protect, for example, against the deterioration of one bit by alpha particle radiation. In this situation, on the 16 lines of the data bus DATA between memory 12 and the SIM 18, only 12 lines will switch (i.e., be active) at the time of the read/write operations by central processing unit 14; the 4 other lines, maintained at a constant logical level, will not induce internal consumption. It will be noted that the bits of the operating code and the bits of the EDCC can either be separated, or interlaced—to improve further the protection.

Regarding zone B of memory 12, it is reserved for the storage of medical data, preferably Holter data. In order to increase the storage capacity, storage of data is made not by words of 16 bits as in the case of zone A, but rather by bytes, separating a 16 bit word into two bytes of 8 bits, one byte having high weight (UB) and the other byte having low weight (LB), for each word stored.

The absence of any EDCC or other logical protection for the information stored in zone B makes it possible in effort to double the storage capacity space 24 of zone B, corresponding to the physical addresses 10000 to 3FFFF, being in fact divided into a first zone 26 containing logical addresses 10000 to 3FFFF and a second zone 28 containing logical addresses 40000 to 6FFFF. The selection of one or the other of zones 26 and 28 is done by application to RAM circuit 12 of a selection signal LB (for zone 26) or UB (for zone 28) at the same time as the selection of write/read signal WR. While reaching thus separately, by the SIM 18, to the 8 bits of low weight or the 8 bits of high weight of the word of 16 bits, one can store two bytes of traditional information per word of 16 bits of the memory. Admittedly, the data do not benefit there from any protection (as contrasted with the operating code stored in zone A), but the accidental loss of such medical data is not critical for the patient or the proper safe functioning of the implant. Nevertheless, one will preferably select for use as a memory circuit one that is protected by a polyimide layer for stopping the alpha particles.

In one embodiment the interface circuit SIM 18 manages the access in reading or writing, to one or the other of the zones A and B of RAM memory 12, as follows: First, for the access in reading in zone A, central processing unit 14 can execute a code stored in ROM 16 or in RAM 12. To execute a code stored in RAM, central processing unit 14 accesses this code stored at a particular address of zone A. During this operation, zone A is protected from writing by microcontroller 10, i.e., any attempt at writing in this zone A would cause a reboot of the system.

Circuit SIM 18 carries out the following operations: First, the SIM 18 reaches in parallel, at the indicated address in zone A, to the operating code (OC, 8 bits) and to the error detection and correction code (EDCC, n=1 to 8 bits). The SIM 18 separates the 8 bits of OC from the n bits of EDCC, with de-interlacing of these bits if necessary. The SIM 18 re-computes the n bits of EDCC starting from the 8 OC bits;

SIM 18 next compares the bits of EDCC calculated with the EDCC bits read from the memory. In the event of identity, the data is considered valid and SIM 18 transmits to CPU 14 the 8 OC bits.

In the event of mismatch, however, SIM 18 corrects, if possible, the error starting from the read EDCC and transmits in real time to CPU 14 the corrected OC. An interruption IT is generated for CPU 14, which recover on this interruption the address of the code where the error was detected as well as the corrected data, these parameters being provided by SIM 18. In part or in whole the zone A is then de-protected from writing, thus allowing a writing the corrected OC word at the address considered. The corrected OC is rewritten at the address indicated via SIM 18, which automatically re-computes the EDCC, adds it to (or interlaces it with) the OC, and physically stores the whole at the address indicated in zone A. One will note that, for security purposes, this specific software procedure for the correction and rewriting is advantageously preserved in ROM 16 of microcontroller 10.

Finally, in the event of a detected error that is not correctable, i.e., generally a plurality of errors on the same word, the SIM 18 generates an indicator, read by central processing unit 14, that in this situation does not execute any more the OC code stored in RAM, but executes a code of fallback (safety code), stored in the ROM 16.

The case of an access in writing in zone A, corresponding to the initial loading, or to an updating, of the software code stored in this zone operates as follows. The role of SIM 18 is to perform the following functions:

(1) calculating the bits of EDCC starting from the OC bits transmitted by central processing unit 14 or the DMA circuit 20 (according to the manner in which the program is to be downloaded);

(2) forming the word containing the 8 bits of operating code and the n bits of EDCC; and (3) writing this formed word, corresponding to the protected code, in zone A of the RAM 12 to the indicated address.

The case of an access in zone B is as follows. Preliminarily, access in zone B is done preferably for readings or writings of Holter data, which in this embodiment consists of data items stored in bytes of 8 bits. As indicated above, the structure of RAM 12 provides access separately to the 8 bits of low weight and the 8 bits of high weight of each word of the zone B, by application of a suitable selection signal UB/LB. In order that this particular organization of the RAM be transparent to central processing unit 14 and the DMA circuit 20, it is necessary that the addresses seen from these circuits (logical addresses) extend from 10000 to 6FFFF, with the zone of the bits of low weight being addressed between 10000 and 3FFFF (addresses always seen from central processing unit 14 or circuit DMA 20) and the zone of the bits of high weight, between addresses 40000 and 6FFFF.

Starting from the addresses seen from the central processing unit 14 or from the DMA circuit 20, SIM 18 re-computes the real address (physical) of the RAM, which is included between 10000 and 3FFFF, and generates corresponding signals UB/LB according to the bits to be addressed, low weight or high weight. This management of the memory, transparent to the central processing unit 14, greatly simplifies the writing of the software for the management of Holter data, because central processing unit 14 "sees" only one continuous addressable space, made up of addresses 10000 to 6FFFF.

Although the embodiments herein describe the invention within the framework of a microcontroller working with an operating code on 8 bits in parallel, it will be understood by a person of ordinary skill in the art that the principle of the invention is of course transposable to a microcontroller of greater power and digital processing capabilities, by choosing, for example, a memory organized in words of 32 bits for a microcontroller 16 bits.

Suitable implantable devices for which the present invention has application include, for example the Symphony, Rhapsody and Alto model devices available from Ela Medical S.A., Montrouge, France. Suitable external ambulatory Holter recorders include Ela Syneflash and SpiderView records also available from Ela Medical. These medical devices and implantable medical devices are microprocessor based systems with memory, data registers and the like (microcontrollers) having circuits for receiving, conditioning and processing detected electrical signals. The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. An active medical device, in particular an implantable active medical device such as a cardiac pacemaker, defibrillator, cardiovertor and/or multisite device, including:
    a microprocessor,
    means for acquiring medical data including Holter data,
    a first memory, for storing a control software for operating the microprocessor, and
    a second memory, for storing the acquired medical data, the first and the second memory being, respectively, a first sector and a second sector of a rewritable single common memory component;
    an interfacing circuit operative to be coupled to said microprocessor and said common memory component;
    characterized in that:
    the microprocessor operates on N bits in parallel and said rewritable memory component is organized to store words of 2N bits;
    said control software is stored in words of 2N bits in the first sector, each one of said words including N bits of operating code forming an instruction for controlling the microprocessor, and n bits of error detection and correction code, with $1 \leq n \leq N$,
    said medical data are formed of elementary data of N bits stored in words of 2N bits in the second sector, each of each said medical data words stored including N bits of high weight, and N bits of low weight;
    said interfacing circuit selectively operating under microprocessor control to:
        read or write in parallel N+n bits of a word of the first sector; or
        read or write N bits of low weight of a word of the second sector, or
        read or write N bits of high weight of a word of the second sector.

2. The device of claim 1, wherein said interface circuit is operable to, after reading of the N+n bits of a word of the first sector:
    analyze the N bits of the operating code and the n bits of the error detection and correction code and check the integrity of said operating code, and
    only in the event of proven integrity, transmit to the microprocessor the N bits of the operating code.

3. The device of-claim 2, wherein said interface circuit is operable to, in response to a not proven integrity of the operating code:
    restore an integrate value of N bits of the operating code based upon the n bits of the error detection and correction code, and
    transmit to the microprocessor the N bits of the operating code thus restored.

4. The device of claim 3 wherein the interface circuit is operable to, in response to a not proven integrity of the operating code:
    re-compute the n bits of the error detection and correction code corresponding to the restored N bits of the operating code, and
    control the microprocessor to rewrite in the first sector the restored N bits of the operating code and the corresponding re-computed n bits of the error detection and correction code.

5. The device of claim 4 further comprising a read-only memory that is distinct from said common memory component, said read only memory containing instructions for controlling the interface circuit in accordance with said aforementioned operations of re-computing and rewriting.

6. The device of claim 3, further comprising means operable in response to a not proven integrity of the operating code and of an inability to restore to an integrate value of N bits of the operating code based upon the n bits of the error detection and correction code for operating said microprocessor in accordance with a fallback software.

7. The device of claim 6, further comprising a read-only memory distinct from said common memory component, containing instructions for controlling said microprocessor for the execution in accordance with said fallback software.

8. The device of claim 1 further comprising:
    means for updating the control software of the microprocessor, means for downloading a sequence of words of N bits of operating instructions of the microprocessor, wherein the interface circuit is operable, for each downloaded word of N bits:

to calculate the n bits of the error detection and correction code corresponding to said N bits, and to write in the first sector said N bits and the corresponding calculated n bits of the error detection and correction code.

9. The device of claim 8 further comprising a read-only memory that is distinct from said common memory component, said read only memory containing instructions for controlling the interface circuit in accordance with said aforementioned operations of calculating and writing.

10. The device of the claim 1, wherein:

in each word of the first sector, the N bits of operating code and the associated n bits of error detection and correction code are stored with mutual interlacing, and said interface circuit is operable, after reading a word stored in the first sector, to de-interlace the N+n bits of a word and provide N bits of operating code and the n bits of error detection and correction code.

11. The device of claim 10, wherein the interface circuit is operable to, in response to a not proven integrity of the operating code:

re-compute the n bits of the error detection and correction code corresponding to the restored N bits of the operating code, and control the microprocessor to rewrite in the first sector the restored N bits of the operating code and the corresponding re-computed n bits of the error detection and correction code and the interface circuit is also operable to interlace N bits restored of the operating code and the re-computed n bits corresponding to the error detection and correction code and rewriting said interfaced bits as a word in the first sector.

12. The device of claim 11 further comprising a read-only memory that is distinct from said common memory component, said read only memory containing instructions for controlling the interface circuit in accordance with said aforementioned operations of re-computing and rewriting.

13. The device of claim 1 further comprises:

a direct memory access circuit co-operating with said interface circuit, wherein said interface circuit is operable, in a selective manner according to a command from said direct memory access circuit:

to read or write N bits of low weight of a word of the second sector, or to read or write N bits of high weight of a word of the second sector, or to read or write N+n bits of the first sector.

14. The device of claim 1, wherein said first memory and the microprocessor are integrated into the same circuit.

15. An active medical device comprising:

means for acquiring medical data including Holter data;

a random access memory having a first sector allocated for storing a control software and a second sector allocated for storing acquired medical data; said memory being a rewritable memory organized to store a plurality of words, each said word having 2N bits, said control software being stored in words of 2N bits in the first sector, each one of said control software words including N bits of operating code forming an instruction for controlling the microprocessor, and n bits of error detection and correction code, with $1 \leq n \leq N$, said medical data being formed of elementary data of N bits stored in words of 2N bits including N bits of high weight and N bits of low weight;

a microprocessor responsive to said control software for performing data processing functions; said microprocessor operating on N bits in parallel and coupled to said medical data acquiring means;

an interfacing circuit operably coupled to said microprocessor and said random access memory component; said interfacing circuit selectively operating under microprocessor control to:

read or write in parallel N+n bits of a word of the first sector; or read or write N bits of low weight of a word of the second sector, or read or write N bits of high weight of a word of the second sector.

16. The device of claim 15, wherein said interface circuit is operable to, after reading of the N+n bits of a word of the first sector:

analyze the N bits of the operating code and the n bits of the error detection and correction code and check the integrity of said operating code, and only in the event of proven integrity, transmit to the microprocessor the N bits of the operating code.

17. The device of claim 16, wherein said interface circuit is operable to, in response to a not proven integrity of the operating code:

restore an integrate value of N bits of the operating code based upon the n bits of the error detection and correction code, and transmit to the microprocessor the N bits of the operating code thus restored.

18. The device of claim 17 wherein the interface circuit is operable to, in response to a not proven integrity of the operating code:

re-compute the n bits of the error detection and correction code corresponding to the restored N bits of the operating code, and control the microprocessor to rewrite in the first sector the restored N bits of the operating code and the corresponding re-computed n bits of the error detection and correction code.

19. The device of claim 18 further comprising a read-only memory containing instructions for controlling the interface circuit in accordance with said aforementioned operations of recomputing and rewriting, said read only memory being a different component than said random access memory.

20. The device of claim 17, further comprising means for operating said microprocessor in accordance with a fallback software, said means being operable in response to a not proven integrity of the operating code and of an inability to restore to an integrate value of N bits of the operating code based upon the n bits of the error detection and correction code; and a read-only memory distinct from said random access memory component containing said fallback software.

21. The device of claim 15 further comprising:

means for downloading a sequence of words of N bits of operating instructions for operating the microprocessor, wherein the interface circuit is operable, in response to each downloaded word of N bits:

to calculate the n bits of the error detection and correction code corresponding to said N bits, and to write in the first sector said N bits downloaded and the corresponding calculated n bits of the error detection and correction code.

22. The device of claim 21 further comprising a read-only memory that is distinct from said random access memory component, said read only memory containing instructions for controlling the interface circuit in accordance with said aforementioned operations of calculating and writing.

23. The device of the claim 15, wherein:
in each word of the first sector, the N bits of operating code and the corresponding n bits of error detection and correction code are stored with mutual interlacing, and
said interface circuit is operable, after reading a word stored in the first sector, to deinterlace the N+n bits of a word and provide N bits of operating code and n bits of error detection and correction code.

24. The device of claim 23, wherein the interface circuit is operable to, in response to a not proven integrity of the operating code:
re-compute the n bits of the error detection and correction code corresponding to the re-stored N bits of the operating code, and
control the microprocessor to rewrite in the first sector the restored N bits of the operating code and the corresponding re-computed n bits of the error detection and correction code and the interface circuit is also operable to interlace N bits restored of the operating code and the re-computed n bits corresponding to the error detection and correction code and rewriting said interfaced bits as a word in the first sector.

25. The device of claim 24 further comprising a read-only memory that is distinct from said random access memory component, said read only memory containing instructions for controlling the interface circuit in accordance with said aforementioned operations of recomputing and rewriting.

26. The device of claim 15 further comprising:
a direct memory access circuit co-operating with said interface circuit,
wherein said interface circuit is operable, in a selective manner according to a command from said direct memory access circuit:
to read or write N bits of low weight of a word of the second sector, or
to read or write N bits of high weight of a word of the second sector, or
to read or write N+n bits of the first sector.

27. The device of claim 15, wherein said random access memory and the microprocessor are integrated in a single circuit component.

* * * * *